US00PP27033P3

(12) United States Plant Patent
Conner

(10) Patent No.: US PP27,033 P3
(45) Date of Patent: Aug. 9, 2016

(54) MUSCADINE GRAPE PLANT NAMED 'GA. 1-1-48'

(50) Latin Name: ***Vitis rotundifolia* Michx.**
Varietal Denomination: Ga. 1-1-48

(71) Applicant: University of Georgia Research Foundation, Inc., Athens, GA (US)

(72) Inventor: Patrick J. Conner, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 70 days.

(21) Appl. No.: 14/544,449

(22) Filed: Jan. 8, 2015

(65) Prior Publication Data

US 2016/0205844 P1 Jul. 14, 2016

(51) Int. Cl.
*A01H 5/08* (2006.01)

(52) U.S. Cl.
USPC ..... Plt./206

(58) Field of Classification Search
USPC ..... Plt./206
See application file for complete search history.

*Primary Examiner* — Annette Para

(74) *Attorney, Agent, or Firm* — Klarquist Sparkman, LLP

(57) ABSTRACT

A new and distinct cultivar of the muscadine grape plant, *Vitis rotundifolia* Michx., named 'Ga. 1-1-48', which has: early ripening berries, typically beginning in the last week of July in Georgia; yellow-green berries; self-fertile flowers; berries that separate with a high percentage of dry stem scars; and berries that are large for a self-fertile cultivar.

2 Drawing Sheets

BRIEF SUMMARY

The present invention comprises a new and distinct plant cultivar of *Vitis rotundifolia* Michx., which has been given the name 'Ga. 1-1-48'. My new variety has been asexually propagated in Tifton, Ga. by rooting cuttings under mist in the summer. The following unique combination of traits have been observed in the original plant of my variety and in asexually propagated progeny, when grown in Georgia, are firmly fixed, and which in combination distinguish it from existing cultivars:

1) Early ripening berries, typically beginning in the last week in July in Georgia.
2) Bright yellow-green berries.
3) Self-fertile flowers.
4) Berries with a dry stem scar that separates cleanly from the pedicel.
5) Berries which are large for a self-fertile cultivar.

Figure 1:
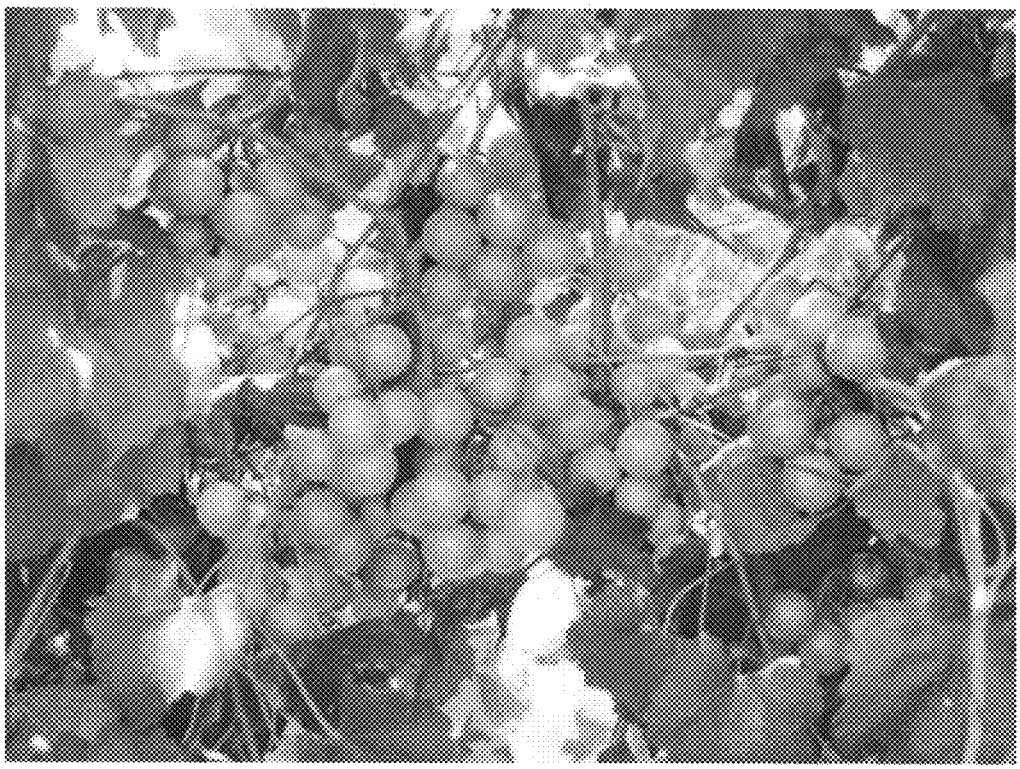
FIG. 1 is a detailed view of several clusters of ripe berries, obtained by clipping away some foliage.

Both Figures show the colors of the new variety as close to true color as is reasonably possible to obtain in colored reproductions of this type. Actual leaf and fruit colors may differ from leaf and fruit colors in the photograph due to light and environmental factors.

DETAILED DESCRIPTION

In the following description, color references are made to The Royal Horticultural Society Colour Chart, copyright 1966, except where general terms of ordinary dictionary significance are used.

BACKGROUND

The muscadine grape, *Vitis rotundifolia* Michx., is a popular fresh fruit grown in the Southeastern United States. In the Georgia climate, many cultivars ripen in early autumn when few other fruits are in season. The berries are large, as compared to other grape species, and are typically borne in clusters of 5-7 berries. Like many fruit crops, muscadine grapes are a heterozygous species and superior genotypes are clonally propagated. Nurseries typically propagate this species either by rooting softwood cuttings under mist, or by layering vines in the field.

The muscadine season in South Georgia begins in the last week of July and first week of August. At this time, growers begin picking the earliest ripening berries on the earliest cultivars. Unlike *vinifera* grapes, fresh-market muscadines are typically harvested as single berries by hand. Muscadines can vary in color from greenish-yellow (bronze) to pink, red, and purple, but stores often segregate them out as either bronze or purple/black. As consumers are often partial to one or the other color, a grower typically would like to have both colors available.

Numerous muscadine cultivars are of commercial importance. One muscadine production guide for Georgia lists 34 fresh market cultivars (nine are categorized as most recommended) and six processed grape cultivars. Even with this large number of cultivars, many are lacking desirable characteristics and growers are very interested in new cultivars with a higher combination of desirable traits. Currently, many commercial vineyards contain primarily female muscadine grape plants with a lesser number of self-fertile cultivars as the pollinator. Female cultivars have a yield that is often only about one-half that of self-fertile cultivars due to lack of pollination (flowers of female cultivars often don't open completely, blocking pollination). Despite the reduced productivity of most female cultivars, growers have continued to grow them because berry size and quality has typically been much larger in female cultivars than in self-fertile cultivars. Generally, growers want a berry size of at least 1 inch (2.5 cm) in diameter in a fresh-market cultivar. Provided minimum size and quality standards are met, more consistently productive self-fertile cultivars would be highly desirable.

Growers are also interested in early season cultivars, especially with dry stem scars.

Therefore, a need exists for an improved muscadine grape cultivar.

DETAILED DESCRIPTION

An initial cross ('Fry'×'Tara') was made by the inventor at the University of Georgia, Tifton Campus as a part of a grape breeding program. 'Fry', the female parent, and 'Tara', the male parent, are both unpatented. One hundred and twenty five seedlings from this cross were germinated in a greenhouse and planted on the Tifton Campus in the spring of 2002. The original seedling vine of 'Ga. 1-1-48' was selected from this group of seedlings. This original 'Ga. 1-1-48' seedling first fruited in 2004 and was selected for propagation because of its self-fertile flowers, early harvest date, excellent fruit flavor, and bright yellow green fruit color. Cuttings were rooted from the selected seedling of this new variety in Tifton, Ga. Asexually propagated plants of the new variety were planted in trial plantings at two locations in Tifton, Ga. and at one location in Wray, Ga. in 2010. A trial planting of asexually propagated plants of the new variety was also made in 2011, in Athens, Ga.

Figure 2:
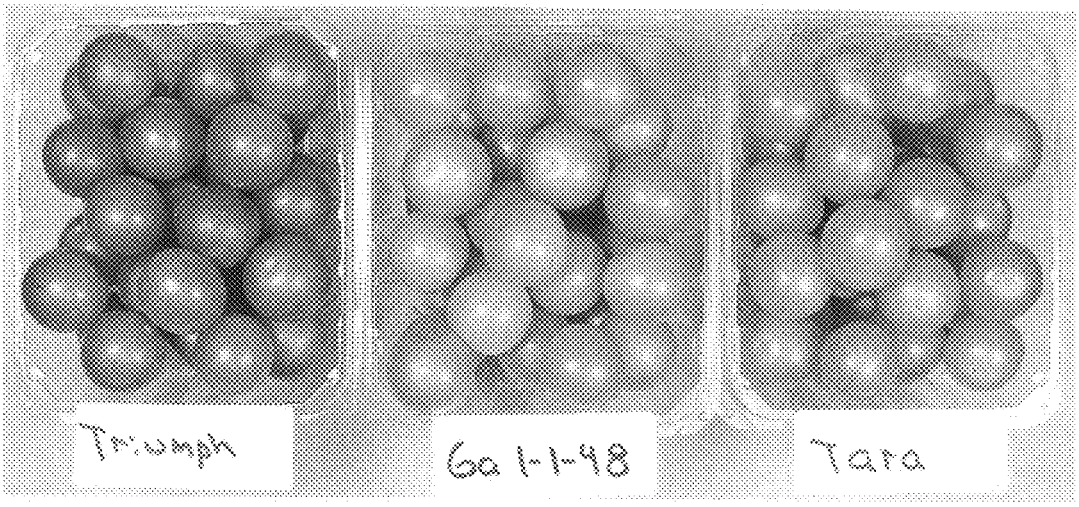
FIG. 2 is a view of ripe 'Ga. 1-1-48' berries (center) in a pint clamshell package in comparison to 'Triumph' (unpatented, left) and 'Tara' (unpatented, right).

'Ga. 1-1-48' is an early season muscadine with yellow-green colored berries (FIG. 2) and self-fertile flowers. Yields of 'Ga. 1-1-48' have been good and are similar to other self-fertile cultivars (see Table 1 below). The quality of 'Ga. 1-1-48' berries is high with exceptionally low levels of splitting and tearing at the pedicel scar (see Table 1 below). First harvest of 'Ga. 1-1-48' in 2012 and 2013 averaged on July 31 (day 212 of the year) at Tifton, Ga., which is similar to other early cultivars and 17 days before the main season parent 'Fry' (see Table 2 below). Berry weight (10.6 g) and diameter (26.2 mm) is similar to other self-fertile cultivars, but smaller than the female parent 'Fry' (see Table 3 below). Soluble solids percentage (14.5) is similar to other cultivars except 'Ga. 5-1-45' (U.S. Plant Pat. No. 24,142), which has exceptional soluble solids. Vine growth as measured by caliper is similar to other muscadine cultivars (see Table 4 below).

PLANT CHARACTERISTICS

Vines: The vines of 'Ga 1-1-48' grow vigorously. For example, the growth of lateral canes on mature vines in Tifton, Ga., has been observed to be about 140 cm per growing season, which is comparable to the growth rate of the male parent 'Tara' and also to 'Ga. 5-1-45'. The trunk caliper measurement at 75 cm above the soil line averaged 33.4 mm for a typical three-year old vine.

Canes: Lateral canes are semi-drooping and usually grow 1 m or more in a season in Georgia. The color of mature canes is greyish brown (RHS 201A) and the bark is smooth. Typical cane diameter is about 2.8 to 11 mm. Internode length ranges from about 2 to 5 cm. Tendrils, averaging about 80 mm in length, are unbranched and discontinuous along the nodes.

Foliage: Leaves average about 10 cm in length and 8.5 cm in width. The leaves are circular with broadly toothed margins and glabrous on both upper and lower surfaces. Mature upper leaf surfaces are dark green (RHS 139A) and somewhat dull, while the lower leaf surfaces are light green (RHS 137B) and shiny. Petiole length equals or slightly exceeds the blade midrib length and the petiole sinus is wide open.

Flowers: The flowers are self-fertile. The petals are yellow green (RHS 145B) and small (with the inflorescence less than about 1 cm in diameter), which is typical for the species. The functional cream-colored anthers (RHS 158A) are supported on long (4 mm) filaments at the base of the ovary. The flowers are short lived, lasting approximately 2 to 3 days. 'Ga 1-1-48' typically blooms from May $10^{th}$ to June $1^{st}$ at Tifton, Ga.

Fruit: The vines produce large, Yellow-green colored fruit (RHS 152D) which ripen in a two-week period beginning around the last week in August in Tifton, Ga. At maturity, the berries weigh approximately 11 g each and average about 15% soluble solids (see Table 4 below). The berries are round and average about 26 mm in diameter (Table 3, Tifton, Ga., 2011-2013), and contain an average of 4 seeds per berry. The seeds are grey brown in color (RHS 152B). The berries have inconspicuous lenticels (too small to obtain a reliable color reading). The berries separate from the pedicel with a relatively dry stem scar, i.e. less than 15% of the berries are torn at the point of detachment from the pedicel (see Table 1 below). The yellow-green color of the 'Ga 1-1-48' fruit is lighter in color than the standard bronze cultivars 'Fry', 'Tara', and 'Triumph' (see Table 5 below).

COMPARISONS WITH OTHER MUSCADINE GRAPE CULTIVARS

The Tables 1-5 below compare 'Ga. 1-1-48' with some other known muscadine grape cultivars. 'Fry', 'Tara' and 'Triumph' are all unpatented. 'Ga. 5-1-45' is the subject of U.S. Plant Pat. No. 24,142.

TABLE 1

Characteristics and Yield (kg/3-m vine), berry quality attributes of 'Ga. 1-1-48' and standard muscadine cultivars at Tifton, Georgia in the third and fourth year of growth (2012, 2013).

| Cultivar | Total Yield (kg)[z] | % Berry rot[zy] | % Pedicel scar split[zx] | % Pedicel scar tear[zw] |
|---|---|---|---|---|
| Year 3 | | | | |
| 'Ga. 1-1-48' | 14.6 b | 23.2 a | 4.0 c | 9.0 b |
| 'Fry' | 11.7 b | 15.3 ab | 34.1 a | 30.7 a |
| 'Ga. 5-1-45' | 12.9 b | 2.8 c | 30.8 a | 29.3 a |
| 'Tara' | 19.1 ab | 19.2 a | 6.4 bc | 15.4 b |
| 'Triumph' | 25.9 a | 4.3 bc | 9.3 b | 34.3 a |
| Significance | 0.021 | 0.011 | <0.001 | 0.003 |
| Year 4 | | | | |
| 'Ga. 1-1-48' | 20.8 ab | 2.6 c | 2.5 d | 5.7 d |
| 'Fry' | 8.7 d | 10.1 b | 13.9 b | 32.8 a |
| 'Ga. 5-1-45' | 13.5 c | 6.0 bc | 24.1 a | 19.4 c |
| 'Tara' | 15.8 bc | 1.6 c | 5.9 cd | 7.5 d |
| 'Triumph' | 24.0 a | 17.9 a | 7.1 c | 26.8 b |
| Significance | <0.001 | <0.001 | <0.001 | <0.001 |

| Cultivar | % Dry pedicel scar[zv] | % Usable yield[zu] | Usable yield (kg)[zu] |
|---|---|---|---|
| Year 3 | | | |
| 'Ga. 1-1-48' | 87.0 a | 73.7 ab | 11.0 b |
| 'Fry' | 35.2 c | 55.9 c | 7.4 b |

TABLE 1-continued

Characteristics and Yield (kg/3-m vine), berry quality attributes of 'Ga. 1-1-48' and standard muscadine cultivars at Tifton, Georgia in the third and fourth year of growth (2012, 2013).

| | | | |
|---|---|---|---|
| 'Ga. 5-1-45' | 40.0 c | 67.2 bc | 8.6 b |
| 'Tara' | 78.2 a | 75.6 ab | 15.1 b |
| 'Triumph' | 56.4 b | 86.8 a | 23.1 a |
| Significance | <0.001 | 0.008 | <0.001 |
| Year 4 | | | |
| 'Ga. 1-1-48' | 91.8 a | 95.0 a | 19.8 a |
| 'Fry' | 53.4 c | 77.7 b | 6.8 c |
| 'Ga. 5-1-45' | 56.5 c | 71.3 b | 9.6 c |
| 'Tara' | 86.5 a | 92.6 a | 14.7 b |
| 'Triumph' | 66.1 b | 76.3 b | 18.3 ab |
| Significance | <0.001 | <0.001 | <0.001 |

[z]Mean separation within columns by Duncan's multiple range test, P < 0.05, with n = 4.
[y]Percentage of berries with visible signs of decay or fungal pathogens.
[x]Percentage of berries which split open at the pedicel scar.
[w]Percentage of berries where the skin tears at the pedicel scar.
[v]Percentage of berries with no splitting or tearing at the pedicel scar after picking.
[u]Usable yield is total yield minus weight of rotted berries and berries with pedicel scar splitting.

TABLE 2

Average first harvest day, and percent yield and percent soluble solid solids of first harvest of 'Ga. 1-1-48' and standard muscadine cultivars at Tifton, Georgia, in the third and fourth year of growth (2012, 2013).

| Cultivar | Avg. day of first harvest (day of year)[z] | % Total yield of first harvest[z] | % Soluble solids of first harvest[z] |
|---|---|---|---|
| 'Ga. 1-1-48' | 212 b | 59.3 | 14.6 |
| 'Fry' | 229 a | 60.8 | 14.2 |
| 'Ga. 5-1-45' | 215 b | 58.3 | 14.6 |
| 'Tara' | 213 b | 46.4 | 13.4 |
| 'Triumph' | 216 b | 40.5 | 14.7 |
| Significance | <0.001 | NS | NS |

[z]Mean separation within columns by Duncan's multiple range test, P < 0.05, with n = 4.
NS = Nonsignificant

TABLE 3

Flower and fruit attributes of 'Ga. 1-1-48' and standard muscadine cultivars at Tifton, Georgia, in years 2011-2013.

| Cultivar | Flower type | Berry color | Berry wt (g)[z] | Berry diam. (mm)[z] | Percent soluble solids of all harvests[z] |
|---|---|---|---|---|---|
| 'Ga. 1-1-48' | SF | Bronze | 10.6 b | 26.2 b | 14.5 a |
| 'Fry' | F | Bronze | 11.9 a | 27.2 a | 14.6 a |
| 'Ga. 5-1-45' | SF | Black | 10.1 bc | 25.9 b | 16.3 a |
| 'Tara' | SF | Bronze | 10.3 bc | 25.7 b | 12.7 b |

TABLE 3-continued

Flower and fruit attributes of 'Ga. 1-1-48' and standard muscadine cultivars at Tifton, Georgia, in years 2011-2013.

| Cultivar | Flower type | Berry color | Berry wt (g)[z] | Berry diam. (mm)[z] | Percent soluble solids of all harvests[z] |
|---|---|---|---|---|---|
| 'Triumph' | SF | Bronze | 9.4 c | 25.1 b | 15.5 a |
| Significance | | | <0.001 | <0.001 | <0.001 |

[z]Mean separation within columns by Duncan's multiple range test, P < 0.05, with n = 4.

TABLE 4

Vine caliper (mm) of Ga. 1-1-48 and standard muscadine cultivars after the first three years of growth at Tifton, Georgia.

| Cultivar | 2011 caliper (mm)[z] | 2012 caliper (mm)[z] | 2013 caliper (mm)[z] |
|---|---|---|---|
| 'Ga. 1-1-48' | 7.2 c | 23.9 | 33.4 |
| 'Fry' | 11.6 a | 26.5 | 35.1 |
| 'Ga. 5-1-45' | 8.4 bc | 22.8 | 30.5 |
| 'Tara' | 10.6 ab | 26.4 | 33.3 |
| 'Triumph' | 9.7 abc | 24.8 | 35.5 |
| Significance | 0.031 | NS | NS |

[z]Caliper measured on the trunk 75 cm above ground before budbreak. Mean separation within columns by Duncan's multiple range test, P < 0.05, with n = 4.
NS = Nonsignificant

TABLE 5

Colorimetric parameters of berry skins of 'Ga. 1-1-48' and standard bronze muscadine cultivars.

| Cultivar | Lightness (L*)[z,y] | Chroma (C*)[x,y] | Hue angle (h°)[w,y] |
|---|---|---|---|
| 'Ga. 1-1-48' | 51.5 a | 15.1 a | 100.9 bc |
| 'Fry' | 46.0 c | 16.4 a | 102.4 b |
| 'Tara' | 48.4 b | 15.0 a | 107.8 a |
| 'Triumph' | 38.6 d | 11.6 b | 98.6 c |
| Significance | <0.001 | <0.001 | <0.001 |

[z]The value of L* describes the degree of darkness or lightness with L = 0 being black and L = 100 white.
[y]Mean separation within columns by Duncan's multiple range test, P < 0.05, with n = 25.
[x]Richness of color is represented by C*
[w]h° represents the dominant color wavelength where 0° = red-purple, 90° = yellow, 180° = bluish-green, 270° = blue.

What is claimed is:

1. A new and distinct muscadine grape plant, substantially as herein illustrated and described, characterized by early ripening berries, typically beginning in the last week of July in Georgia; yellow-green berries; self-fertile flowers; berries that separate with a high percentage of dry stem scars; and berries that are large for a self-fertile cultivar.

* * * * *